United States Patent
Wu et al.

(10) Patent No.: US 11,445,722 B2
(45) Date of Patent: Sep. 20, 2022

(54) TUMOR TISSUE CRYOPRESERVATION KIT, TUMOR TISSUE RESUSCITATION KIT, AND METHOD OF CRYOPRESERVING AND/OR RESUSCITATING TUMOR TISSUE

(71) Applicant: SHANGHAI CELLIVER BIOTECHNOLOGY INC., Shanghai (CN)

(72) Inventors: Hongping Wu, Shanghai (CN); Min Zeng, Shanghai (CN); Xu Zhou, Shanghai (CN); Xiaofang Jin, Shanghai (CN); Qiurui Yang, Shanghai (CN)

(73) Assignee: SHANGHAI CELLIVER BIOTECHNOLOGY INC., Shanghai (CN)

( * ) Notice: Subject to any disclaimer, the term of this patent is extended or adjusted under 35 U.S.C. 154(b) by 969 days.

(21) Appl. No.: 16/199,266

(22) Filed: Nov. 26, 2018

(65) Prior Publication Data
US 2019/0090475 A1    Mar. 28, 2019

Related U.S. Application Data

(63) Continuation-in-part of application No. PCT/CN2017/075579, filed on Mar. 3, 2017.

(30) Foreign Application Priority Data

May 25, 2016  (CN) .......................... 201610356737.6

(51) Int. Cl.
*A01N 1/02* (2006.01)
*C12N 5/09* (2010.01)
*C12N 5/00* (2006.01)
*G01N 1/06* (2006.01)

(52) U.S. Cl.
CPC ......... *A01N 1/0221* (2013.01); *A01N 1/0231* (2013.01); *A01N 1/0242* (2013.01); *A01N 1/0268* (2013.01); *A01N 1/0278* (2013.01); *A01N 1/0284* (2013.01); *C12N 5/0018* (2013.01); *C12N 5/0693* (2013.01); *C12N 2523/00* (2013.01); *C12N 2533/78* (2013.01); *G01N 1/06* (2013.01)

(58) Field of Classification Search
None
See application file for complete search history.

(56) References Cited

U.S. PATENT DOCUMENTS

2017/0087230 A1*  3/2017  Genin .................. A61K 9/0019

OTHER PUBLICATIONS

Balci D. et al. The Assessment of Cryopreservation Conditions for Human Umbilical Cord Stroma-Derived Mesenchymal Stem Cells . . . Current Stem Cell Research & Therapy 8(2)60-72 2013. (Year: 2013).*

* cited by examiner

*Primary Examiner* — Ralph J Gitomer
(74) *Attorney, Agent, or Firm* — Matthias Scholl P.C.; Matthias Scholl

(57) ABSTRACT

A kit, including: a first solution, a second solution, and a metal mesh. The first solution includes: dulbecco's modified eagle medium (DMEM), 65-95 V/V %; dimethyl sulfoxide (DMSO), 5.5-20 V/V %; ethylene glycol (EG), 3.5-15 V/V %; bovine serum albumin (BSA), 0.5-4 W/V %; sucrose 1-5 W/V %; methylcellulose with a viscosity of 4000 centipoise (cP), 0.05-0.8 W/V %; hetastarch 0.25-0.6 W/V %; and glucose 15-35 W/V %. The second solution includes: DMEM, 65-95 V/V %; DMSO, 5.5-20 V/V %; EG, 8-20 V/V %; BSA, 0.5-4 W/V %; sucrose, 10-20 W/V %; methylcellulose with a viscosity of 4000 centipoise (cP), 0.05-0.8 W/V %; polyvinyl pyrrolidone (PVP), 0.25-0.6 W/V %; and glucose 15-35 W/V %. The metal mesh has a thickness of 0.15-0.2 mm and includes a plurality of square holes. The side length of the square holes is 2.0-3.0 mm, and the spacing between adjacent holes is 0.5-2.0 mm.

5 Claims, 5 Drawing Sheets

TUMOR TISSUE CRYOPRESERVATION KIT, TUMOR TISSUE RESUSCITATION KIT, AND METHOD OF CRYOPRESERVING AND/OR RESUSCITATING TUMOR TISSUE

CROSS-REFERENCE TO RELATED APPLICATIONS

This application is a continuation-in-part of International Patent Application No. PCT/CN2017/075579 with an international filing date of Mar. 3, 2017, designating the United States, now pending, and further claims foreign priority benefits to Chinese Patent Application No. 201610356737.6 filed May 25, 2016. The contents of all of the aforementioned applications, including any intervening amendments thereto, are incorporated herein by reference. Inquiries from the public to applicants or assignees concerning this document or the related applications should be directed to: Matthias Scholl P C., Attn.: Dr. Matthias Scholl Esq., 245 First Street, 18th Floor, Cambridge, Mass. 02142.

BACKGROUND

This disclosure relates to a tumor tissue cryopreservation kit, a tumor tissue resuscitation kit, and a method of using the same.

Patient-derived xenografts (PDXs) are models of cancer where the tissue or cells from a patient's tumor are implanted into an immunodeficient mouse. PDX models are used to create an environment that allows for the growth and monitoring of cancer cells, and for evaluation of the treatment progress. However, the PDXs model building is complex, costly, and time-consuming.

Cryoconservation of animal tumor tissue is a strategy where tumor samples are preserved cryogenically. Traditional cryopreservation relies on coating the material to be frozen with cryoprotectants. However, the cryoprotectants are often toxic and themselves may impact the structure and function of the cancer cells.

SUMMARY

Disclosed is a tumor tissue cryopreservation kit, a tumor tissue resuscitation kit, a tumor tissue cryopreservation method and a tumor tissue resuscitation method.

In a first aspect of the disclosure, a tumor tissue cryopreservation kit is provided, the kit comprising:
- a first solution, comprising: dulbecco's modified eagle medium (DMEM), 65-95 V/V %; dimethyl sulfoxide (DMSO), 5.5-20 V/V %; ethylene glycol (EG), 3.5-15 V/V %; bovine serum albumin (BSA), 0.5-4 W/V %; sucrose 1-5 W/V %; methylcellulose with a viscosity of 4000 centipoise (cP), 0.05-0.8 W/V %; hetastarch 0.25-0.6 W/V %; glucose 15-35 W/V %;
- a second solution, comprising: DMEM, 65-95 V/V %; DMSO, 5.5-20 V/V %; EG, 8-20 V/V %; BSA, 0.5-4 W/V %; sucrose, 10-20 W/V %; methylcellulose with a viscosity of 4000 centipoise (cP), 0.05-0.8 W/V %; polyvinyl pyrrolidone (PVP), 0.25-0.6 W/V %; glucose 15-35 W/V %; and
- a metal mesh, with a thickness of 0.15-0.2 mm, and comprising a plurality of square holes, a side length of the square holes being 2.0-3.0 mm, and a spacing between adjacent holes being 0.5-2.0 mm.

The first solution can comprise: dulbecco's modified eagle medium (DMEM), 80 V/V %; dimethyl sulfoxide (DMSO), 10 V/V %; ethylene glycol (EG), 10 V/V %; bovine serum albumin (BSA), 3 W/V %; sucrose 1 W/V %; methylcellulose with a viscosity of 4000 centipoise (cP), 0.05 W/V %; hetastarch 0.25 W/V %; glucose 25 W/V %.

The second can comprise: DMEM, 70 V/V %; DMSO, 18 V/V %; EG, 12 V/V %; BSA, 3 W/V %; sucrose, 20 W/V %; methylcellulose with a viscosity of 4000 centipoise (cP), 0.05 W/V %; PVP, 0.25 W/V %; glucose 30 W/V %.

The kit can further comprise a slicer; the slicer can comprise a pedestal; the pedestal can comprise an upper surface, a recessed portion disposed on the upper surface, and a plurality of guiding grooves which can be equidistantly distributed and vertically downward from the upper surface of the pedestal; and the depth of the plurality of guiding grooves can be greater than the depth of the recessed portion.

The depth of the plurality of guiding grooves can be greater than the depth of the recessed portion by 1.8-2.3 mm, and the spacing between two adjacent guiding grooves can be 1 mm.

The recessed portion can be an ellipsoid with the width of 16 mm and the length of 25 mm; and the vertical distance from the lowest point of the recessed portion to the upper surface of the pedestal can be 8.5 mm.

In a second aspect of the disclosure, a tumor tissue resuscitation kit is provided, the kid comprising:
- a first solution, comprising: dulbecco's modified eagle medium (DMEM), 65-85 V/V %; phosphate buffer saline (1×), 15-35 V/V %; bovine serum albumin (BSA), 1-3 W/V %; sucrose 10-40 W/V %; glucose, 15-35 W/V %;
- a second solution, comprising: dulbecco's modified eagle medium (DMEM), 65-85 V/V %; phosphate buffer saline (1×), 15-35 V/V %; bovine serum albumin (BSA), 1-3 W/V %; sucrose 10-20 W/V %; glucose, 15-35 W/V %; and
- a third solution, comprising: dulbecco's modified eagle medium (DMEM), 75-95 V/V %; phosphate buffer saline (1×), 5-25 V/V %; bovine serum albumin (BSA), 1-3 W/V %; glucose, 15-35 W/V %.

Further, the first solution can comprise: dulbecco's modified eagle medium (DMEM), 65 V/V %; phosphate buffer saline (1×), 35 V/V %; bovine serum albumin (BSA), 2 W/V %; sucrose 40 W/V %; glucose, 25 W/V %.

Further, the second solution can comprise: dulbecco's modified eagle medium (DMEM), 75 V/V %; phosphate buffer saline (1×), 25 V/V %; bovine serum albumin (BSA), 2 W/V %; sucrose 20 W/V %; glucose, 25 W/V %.

Further, the third solution can comprise: dulbecco's modified eagle medium (DMEM), 95 V/V %; phosphate buffer saline (1×), 5 V/V %; bovine serum albumin (BSA), 2 W/V %; glucose, 15 W/V %.

In a third aspect of the disclosure, a method for cryopreserving tumor tissue using the cryopreservation kit as above is provided, the method comprising:
1) providing a tumor tissue, washing the tumor tissue with physiological saline, removing a blood vessel, a capsule, and a necrotic tissue of the tumor tissue, slicing the tumor tissue to yield slices of the tumor tissue, and washing the slices of the tumor tissue with physiological saline;
2) immersing the slices of the tumor tissue in the first solution of the cryopreservation kit for 20-30 min;
3) immersing the slices of the tumor tissue in the second solution of the cryopreservation kit for 10-20 min;
4) taking the slices of the tumor tissue out of the second solution, placing the slices on the metal mesh of the cryopreservation kit, immersing the metal mesh in liquid nitrogen for at least 5 minutes; and 5) storing the tumor tissue in a liquid nitrogen tank.

The metal mesh can be made of metal sheet with a thickness of 0.15-0.2 mm. Two rows of square holes are distributed on the metal mesh. The side length of the square hole is 2.5 mm, and the spacing between adjacent holes is 1 mm.

Further, in 1), the tumor tissue can be sliced into a size of 1×5×5 mm.

Further, in 2), the slices of the tumor tissue can be immersed in 10 mL of the first solution for 25 min at room temperature.

Further, in 3), the slices of the tumor tissue can be immersed in 10 mL of the second solution for 15 min at room temperature.

In a fourth aspect of the disclosure, a method for resuscitating tumor tissue using the resuscitation kit as above is provided, the method comprising:

1) taking a tumor tissue out of a liquid nitrogen tank, and immersing the tumor tissue in the first solution of the resuscitation kit for 2-5 min at a temperature of 36-38° C.;
2) taking the tumor tissue out of the first solution and immersing the tumor tissue in the second solution of the resuscitation kit for 3-8 min;
3) taking the tumor tissue out of the second solution and immersing the tumor tissue in the third solution of the resuscitation kit for 8-15 min; and
4) preparing the third solution of the kit, and transferring and immersing the tumor tissue treated in 3) to the third solution for 10 min.

Further, in 1), the tumor tissue can be immersed in 10 mL of the first solution of the resuscitation kit for 3 min at the temperature of 37° C.

Further, in 2), the tumor tissue can be immersed in the second solution of the resuscitation kit for 5 min at room temperature.

Further, in 3), the tumor tissue can be immersed in 10 mL of the third solution of the resuscitation kit for 10 min at room temperature.

The kits can resuscitate the cryopreserved tumor tissue by more than 85%. The cryopreserved and resuscitated tumor tissues have the same histological and genetic characteristics as the fresh tumor tissues and maintain the heterogeneity of the tumors.

The solutions of the kits contain permeable and non-permeable cryoprotectant, and can prevent the growth of ice crystals.

The cryopreservation system of the kits balances the toxicity, permeability and vitrification efficiency of the cryoprotectant, thus preventing the rapid crystallization of the tumor tissue.

The kits protect the tissue in low temperature environment, so that the tumor tissue can temporarily get out of the growth state to keep primary characteristics, and can be prepared, preserved, and applied at any time. The preservation method is labor-saving, easy to operate, and low in cost.

In a fifth aspect of the disclosure, a tumor tissue cryopreservation-resuscitation combined kit is provided. The kit comprises the tumor tissue cryopreservation kit as described above and the tumor tissue resuscitation kit as described above.

In a sixth aspect of the disclosure, a method for cryopreserving and resuscitating tumor tissue using the kits is provided. The method is a combination of the tumor tissue cryopreservation method as described above and the tumor tissue resuscitation method as described above.

The combination of the tumor tissue cryopreservation kit with the tumor tissue resuscitation kit can better preserve the original characteristics of the tumor tissue and the morphology of the primary tumor, and improve the survival rate.

BRIEF DESCRIPTION OF THE DRAWINGS

FIG. 4A represents the H&E staining result of fresh tumor tissue, FIG. 4B represents the H&E staining result of cryopreserved-rewarmed tumor tissue (Example 7);

FIG. 5A is a perspective view, FIG. 5B is a top view, and FIG. 5C is a cross-sectional view in the A-A direction.

DETAILED DESCRIPTION

Figure 1A:
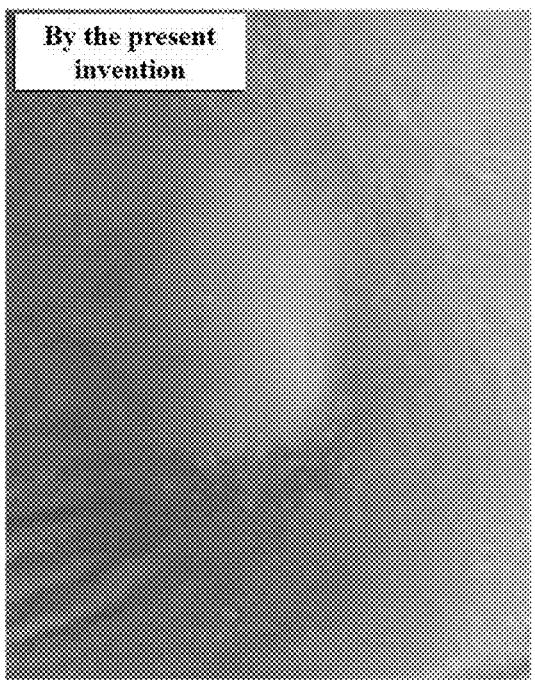
FIGS. 1A-1B are diagrams illustrating the modeling of PDXs after one month of implantation in immunodeficient mice with human primary cholangiocarcinoma tumor tissue cryopreserved according to one embodiment of the disclosure and the conventional cryopreservation method (Example 6)

To further illustrate, examples detailing a tumor tissue cryopreservation kit and a tumor tissue resuscitation kit are described below. It should be noted that the following examples are intended to describe and not to limit the description.

Example 1: Preparation of Tumor Tissue Cryopreservation Kit

The formulation components of the solutions for tumor tissue cryopreservation kit are as follows:

A first solution (V1), comprising: dulbecco's modified eagle medium (DMEM), 65-95 V/V %; dimethyl sulfoxide (DMSO), 5.5-20 V/V %; ethylene glycol (EG), 3.5-15 V/V %; bovine serum albumin (BSA), 0.5-4 W/V %; sucrose 1-5 W/V %; methylcellulose with a viscosity of 4000 centipoise (cP), 0.05-0.8 W/V %; hetastarch 0.25-0.6 W/V %; glucose 15-35 W/V %. Specifically, in this example, the first solution comprises: DMEM 80 V/V %, DMSO 10 V/V %, EG 10 V/V %, BSA 3 W/V %, sucrose 1 W/V %, methylcellulose 4000 cP 0.05 W/V %, hetastarch 0.25 W/V %, glucose 25 W/V %; and A second solution (V2), comprising: DMEM, 65-95 V/V %; DMSO, 5.5-20 V/V %; EG, 8-20 V/V %; BSA, 0.5-4 W/V %; sucrose, 10-20 W/V %; methylcellulose with a viscosity of 4000 centipoise (cP), 0.05-0.8 W/V %; polyvinyl pyrrolidone (PVP), 0.25-0.6 W/V %; glucose 15-35 W/V %. Specifically, in this example, the first solution comprises: DMEM 70 V/V %, DMSO 18 V/V %, EG 12 V/V %, BSA 3 W/V %, sucrose 20 W/V %, methylcellulose 4000 cP 0.05 W/V %, PVP 0.25 W/V %, glucose 30 W/V %.

The English name and the manufacturer of each reagent are as follows:

DMEM: dulbecco's modified eagle medium (high glucose); Sigma-Aldrich.
DMSO: dimethyl sulfoxide; Sigma-Aldrich.
BSA: Bovine Serum Albumin; Sigma-Aldrich.
EG: Ethylene Glycol; Sigma-Aldrich.
Sucrose: Sigma-Aldrich.
methylcellulose 4000 cP: Sigma-Aldrich.
hetastarch: Sigma-Aldrich.
glucose: Sigma-Aldrich.
PVP: Polyvinyl Pyrrolidone; Sigma-Aldrich.

Example 2: Method of Cryopreserving Tumor Tissue

The prepared cryopreservation kit is filtered, packaged, and stored temporarily in a refrigerator at −4° C., and stored in a refrigerator at −20° C. for long-term preservation.

The method of cryopreserving tumor tissue are as follows:

a. The tumor tissue is washed three times with physiological saline. The blood vessel, the capsule, and the necrotic tissue are trimmed and peeled off, and the tumor tissue is sliced with the slicer into a size of 1×10×10 mm, and washed again with physiological saline.

Figure 5A:
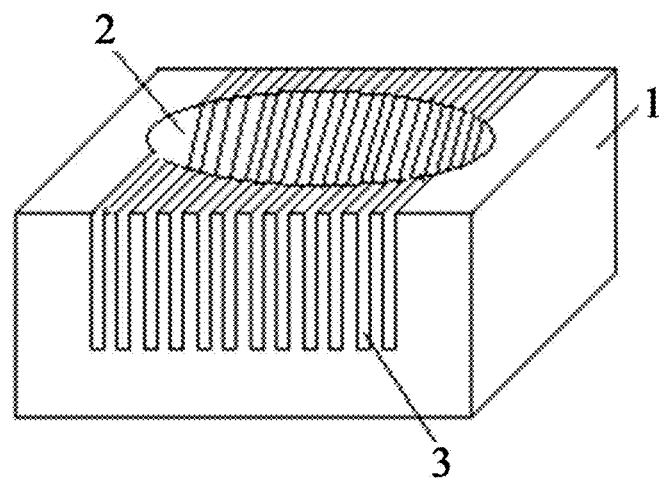
FIGS. 5A-5C are diagrams illustrating a tumor tissue slicer of a tumor tissue cryopreservation kit as described in the disclosure.
Figure 5B:
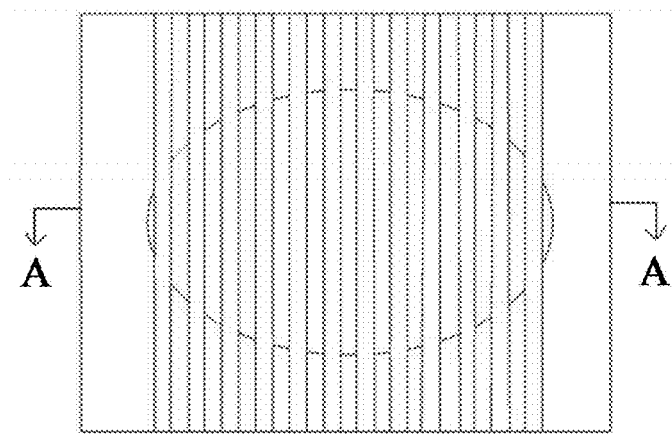
Figure 5C:
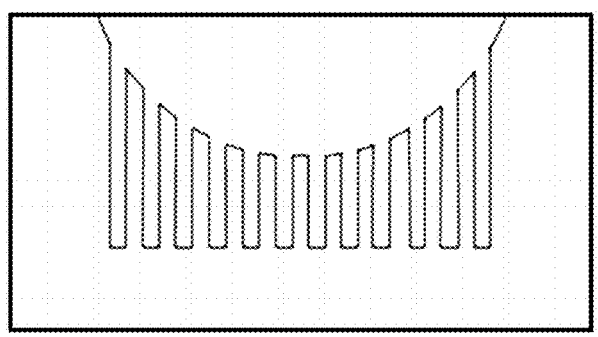
Figure 6:
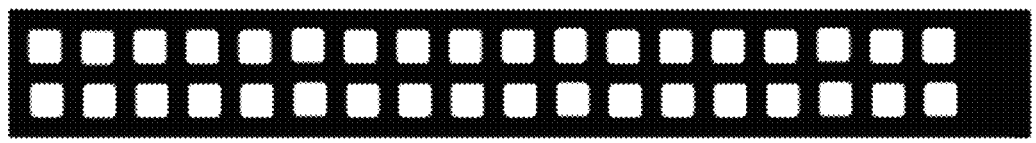
FIG. 6 is a diagram illustrating a front view of the metal mesh of a tumor tissue cryopreservation kit as described in the disclosure.

The slicer, as shown in FIGS. 5A-5C, comprises: a pedestal 1 comprising an upper surface and a recessed portion 2 formed on the upper surface; twelve guiding grooves 3, which are equidistantly distributed and have a depth 2 mm deeper than the lowest point of the recessed portion 2, are vertically downward from the upper surface of the pedestal 1. The spacing between the two adjacent guiding grooves 3 is 1 mm. The recessed portion 2 is an ellipsoid with a width of 16 mm and a length of 25 mm; and a vertical distance from the lowest point of the recessed portion 2 to the upper surface of the pedestal 1 is 8.5 mm.

b. The first solution (V1) and the second solution (V2) are prepared, and then filtered to eliminate bacteria;

c. the tumor tissue slices are immersed in 10 mL of the V1 at room temperature for 25 min;

d. the tumor tissue slices are immersed in 10 mL of the V2 at room temperature for 15 min, or until they precipitate to the bottom of the tube; and e. the tumor tissue slices are placed in a minimum volume of solution onto a metal mesh (as shown in FIG. 6), and immersed directly into liquid nitrogen for at least 5 minutes; and f. the metal mesh with tumor tissue slices is inserted into a marked cryotube, and stored in a liquid nitrogen tank for long-term preservation.

Example 3: Preparation of Tumor Tissue Resuscitation Kit

The formulation components of the solutions for tumor tissue resuscitation kit are as follows:

Solution 1 (T1), comprising: dulbecco's modified eagle medium (DMEM), 65-85 V/V %; phosphate buffer saline (1×), 15-35 V/V %; bovine serum albumin (BSA), 1-3 W/V %; sucrose 10-40 W/V %; glucose, 15-35 W/V %; specifically, in this example, the Solution 1 (T1) comprises: DMEM 65 V/V %, 1×PBS 35 V/V %, BSA 2 W/V %, sucrose 40 W/V %, glucose 25 W/V %;

Solution 2 (T2), comprising: dulbecco's modified eagle medium (DMEM), 65-85 V/V %; phosphate buffer saline (1×), 15-35 V/V %; bovine serum albumin (BSA), 1-3 W/V %; sucrose 10-20 W/V %; glucose, 15-35 W/V %; specifically, in this example, the Solution 2 (T2) comprises: DMEM 75 V/V %, 1×PBS 25 V/V %, BSA 2 W/V %, sucrose 20 W/V %, glucose 25 W/V %; and Solution 3 (T3), comprising: dulbecco's modified eagle medium (DMEM), 75-95 V/V %; phosphate buffer saline (1×), 5-25 V/V %; bovine serum albumin (BSA), 1-3 W/V %; glucose, 15-35 W/V %. Specifically, in this example, the Solution 3 (T3) comprises: DMEM 95 V/V %, 1×PBS 5 V/V %, BSA 2 W/V %, glucose 15 W/V %.

The English name and the manufacturer of each reagent are as follows:

DMEM: dulbecco's modified eagle medium (high glucose); Sigma-Aldrich.
1×PBS: 0.01M Phosphate Buffered Saline; Sigma-Aldrich.
BSA: Bovine Serum Albumin; Sigma-Aldrich.
Sucrose: Sigma-Aldrich.
glucose: Sigma-Aldrich.

Example 4: Method of Resuscitating Tumor Tissue

The method for resuscitating tumor tissue are as follows:

a. The tumor tissue slices are taken out of the liquid nitrogen tank and immersed into 10 mL of the T1 at 37° C. for 3 min;

b. the tumor tissue slices are immersed into 10 mL of the T2 at room temperature for 5 min;

c. the tumor tissue slices are immersed into 10 mL of the T3 at room temperature for 10 min; and d. the tumor tissue slices are immersed into 10 mL of fresh T3 at room temperature for 10 min; the resuscitated tumor tissue is obtained and can be used in subsequent studies.

Example 5: Cryopreservation of Human Primary Cholangiocarcinoma Tumor Tissue a. The human primary cholangiocarcinoma tumor tissue is washed three times with physiological saline. The blood vessel, the capsule, and the necrotic tissue are trimmed and peeled off, and the tumor tissue is sliced with the slicer into a size of 1×10×10 mm, and washed again with physiological saline;

b. the first solution (V1), the second solution (V2), solution 1 (T1), solution 2 (T2) and solution 3 (T3) are prepared, and then filtered to eliminate bacteria;

c. the tumor tissue slices are immersed in 10 mL of the V1 at room temperature for 25 min;

d. the tumor tissue slices are immersed in 10 mL of the V2 at room temperature for 15 min, or until they precipitate to the bottom of the tube;

e. the tumor tissue slices are placed in a minimum volume of solution onto a metal mesh, and immersed directly into liquid nitrogen for at least 5 minutes; and f. the metal mesh with tumor tissue slices is inserted into a marked cryotube, and stored in a liquid nitrogen tank for long-term preservation.

Example 6: Resuscitation of Human Primary Cholangiocarcinoma Tumor Tissue a. The tumor tissue slices are taken out of the liquid nitrogen tank and immersed into 10 mL of the T1 at 37° C. for 3 min;

b. the tumor tissue slices are immersed into 10 mL of the T2 at room temperature for 5 min;

c. the tumor tissue slices are immersed into 10 mL of the T3 at room temperature for 10 min;

d. the tumor tissue slices are immersed into 10 mL of fresh T3 at room temperature for 10 min; and the resuscitated tumor tissue is obtained;

e. the resuscitated tumor tissue can be transplanted to immunodeficient mice to establish a new generation of PDX model for subsequent medical or scientific research after being washed with physiological saline.

Figure 1B:
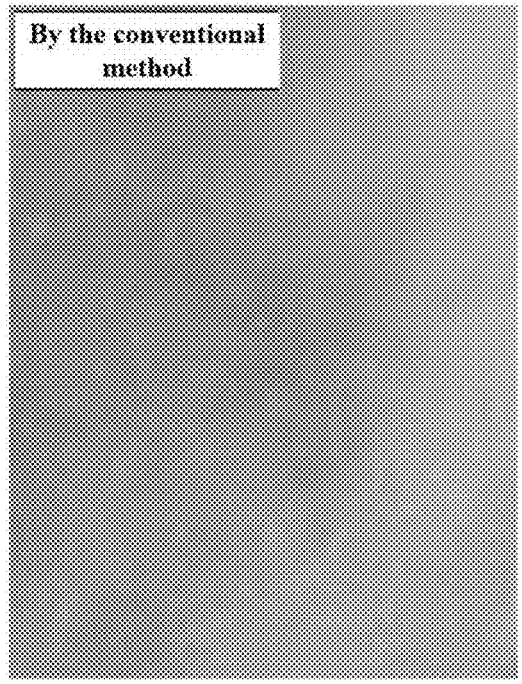

As shown in FIGS. 1A-1B, the human primary cholangiocarcinoma tumor tissue is cryopreserved and resuscitated by the method as described in the disclosure or the conventional method, and then transplanted to immunodeficient mice for one month. It can be seen that the tumor of the experimental group using the method as described in the disclosure still exists, the progressive growth is distinct, so the PDX modeling is successful; while the tumor of the control group using the conventional method disappears, leaving only a slight scar tissue, which means PDX modeling failed. Results: The human primary cholangiocarcinoma tumor tissue, cryopreserved and resuscitated by the kit and the method as described in the disclosure, can be successfully transplanted to immunodeficient mice to establish an effective PDX mouse model. However, using the conventional method to cryopreserve and resuscitate tumor tissue, the PDX model could not be established in immunodeficient mice.

Figure 2:
FIG. 2 is a diagram illustrating the anatomy of PDXs tumor derived from the cryopreserved-rewarmed human primary cholangiocarcinoma tumor tissue after one month of implantation in immunodeficient mice (Example 6)

As shown in FIG. 2, the anatomy of human primary cholangiocarcinoma tumor tissue, cryopreserved, resuscitated and transplanted to immunodeficient mice for one month, shows that the tumor tissue forms new vessels, and progressively proliferated and enlarged.

Results: The human primary cholangiocarcinoma tumor tissue, cryopreserved and resuscitated by the kit and the method as described in the disclosure, can be transplanted to immunodeficient mice to establish a PDX mouse model successfully, and the tumor tissue is activated in the mouse.

Figure 3:
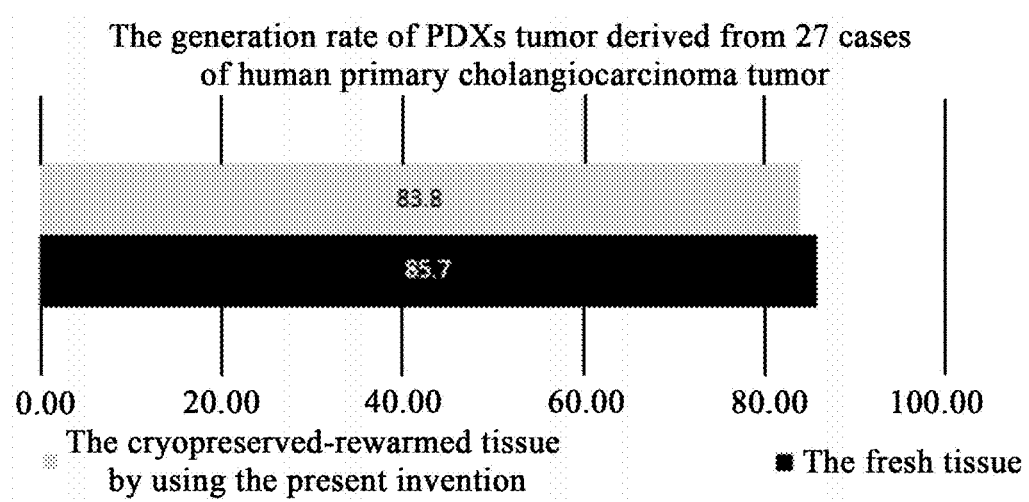
FIG. 3 is a diagram illustrating the comparative percent bar chart of PDXs tumor generation rate derived from fresh and cryopreserved-rewarmed human primary cholangiocarcinoma tumor tissue (Example 6)

As shown in FIG. 3, 27 cases of human primary cholangiocarcinoma tumor tissue are cryopreserved and resuscitated by the kits as described in the disclosure, and then transplanted to immunodeficient mice. Compared with the fresh tissue, the formation rate of transplanted tumor of the two are both about 85%. Results: Compared with the fresh ones, the human primary cholangiocarcinoma tumor tissue, cryopreserved and resuscitated by the kit and the method as described in the disclosure, showed no significant difference in the success rate of transplanting tumor formation.

Example 7: Hematoxylin-Eosin Staining (H&E Staining) Experiment of Human Primary Cholangiocarcinoma Tumor Tissue after Cryopreservation and Resuscitation Experimental Method Tumor tissue is cryopreserved, resuscitated, fixed with 4% paraformaldehyde, embedded in paraffin, sliced using conventional paraffin, dewaxed (first xylene 3-5 min, second xylene 3-5 min, 100% ethanol 1-2 min, first 95% ethanol 1-2 min, second 95% ethanol 1-2 min, 80% ethanol 1 min, 70% ethanol 1 min), rinsed with tap water, rinsed with distilled water, dyed using hematoxylin for 3-10 min, rinsed with tap water, differentiated using 1% hydrochloric acid and alcohol for 3-5 sec, rinsed with tap water, saturated lithium carbonate solution for 1-2 min, tap water for 15 min, soaked in 0.5% eosin solution for 1-2 min, dehydrated (first 95% ethanol 1-2 min, second 95% ethanol 1-2 min, 100% ethanol 1-2 min), hyalinized (xylene-carbolic acid mixture 2 min, first xylene 1-2 min, second xylene 1-2 min, third xylene 1-2 min), and sealed using neutral balsam seal. Observe the resulting product under microscope, and take photos.

Experimental Result

Figure 4A:
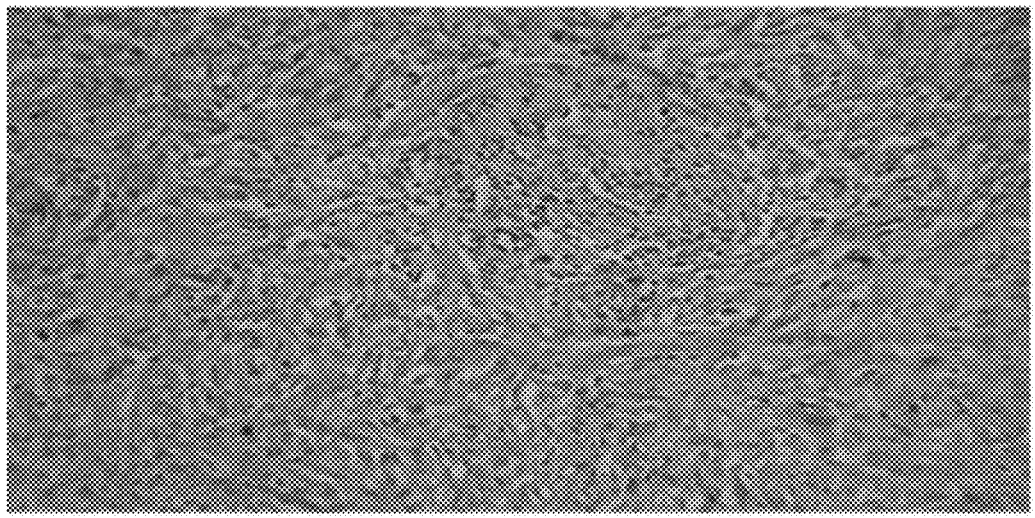
FIGS. 4A-4B are diagrams illustrating the comparison of the results of H&E staining of fresh or cryopreserved-rewarmed tumor tissue.
Figure 4B:
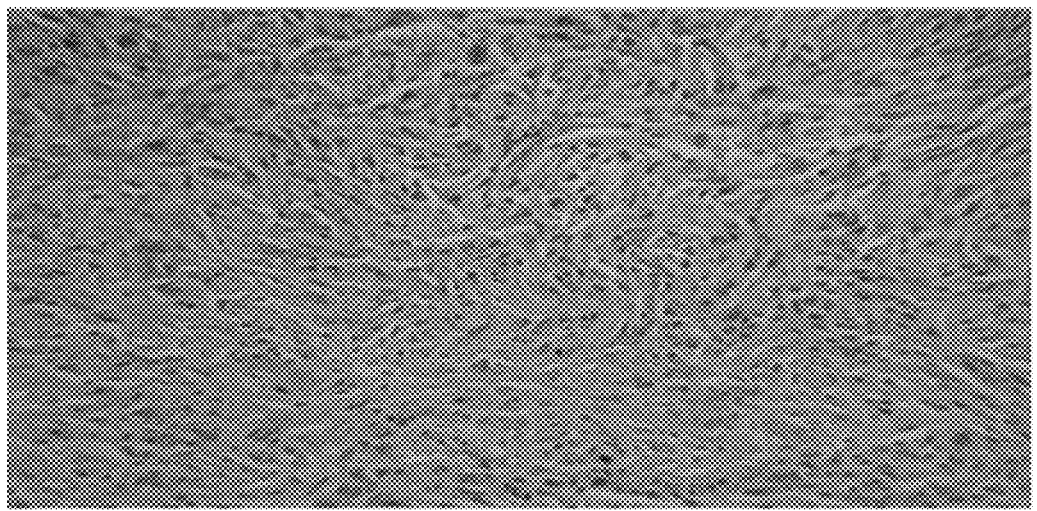

FIG. 4A represents the H&E staining result of fresh tumor tissue, and FIG. 4B represents the H&E staining result of the cryopreserved-rewarmed tumor tissue, showing that the cryopreserved-rewarmed tumor tissue has a similar morphological structure to the fresh one, suggesting that the cryopreservation and resuscitation processes do not affect tumor characteristics significantly. The results indicate that the cryopreservation and resuscitation processes do not significantly affect tumor characteristics.

It will be obvious to those skilled in the art that changes and modifications may be made, and therefore, the aim in the appended claims is to cover all such changes and modifications.

What is claimed is:

1. A kit, comprising:
   a first solution, comprising: dulbecco's modified eagle medium (DMEM), 65-95 V/V %; dimethyl sulfoxide (DMSO), 5.5-20 V/V %; ethylene glycol (EG), 3.5-15 V/V %; bovine serum albumin (BSA), 0.5-4 W/V %; sucrose 1-5 W/V %; methylcellulose with a viscosity of 4000 centipoise (cP), 0.05-0.8 W/V %; hetastarch 0.25-0.6 W/V %; glucose 15-35 W/V %;
   a second solution, comprising: DMEM, 65-95 V/V %; DMSO, 5.5-20 V/V %; EG, 8-20 V/V %; BSA, 0.5-4 W/V %; sucrose, 10-20 W/V %; methylcellulose with a viscosity of 4000 centipoise (cP), 0.05-0.8 W/V %; polyvinyl pyrrolidone (PVP), 0.25-0.6 W/V %; glucose 15-35 W/V %; and
   a metal mesh, with a thickness of 0.15-0.2 mm, and comprising a plurality of square holes, a side length of the square holes being 2.0-3.0 mm, and a spacing between adjacent holes being 0.5-2.0 mm.

2. The kit of claim 1, wherein:
   the first solution comprises: dulbecco's modified eagle medium (DMEM), 80 V/V %; dimethyl sulfoxide (DMSO), 10 V/V %; ethylene glycol (EG), 10 V/V %; bovine serum albumin (BSA), 3 W/V %; sucrose 1 W/V %; methylcellulose with a viscosity of 4000 centipoise (cP), 0.05 W/V %; hetastarch 0.25 W/V %; glucose 25 W/V %; and
   the second solution comprises: DMEM, 70 V/V %; DMSO, 18 V/V %; EG, 12 V/V %; BSA, 3 W/V %; sucrose, 20 W/V %; methylcellulose with a viscosity of 4000 centipoise (cP), 0.05 W/V %; PVP, 0.25 W/V %; glucose 30 W/V %.

3. The kit of claim 1, further comprising a slicer; wherein the slicer comprises a pedestal; the pedestal comprises an upper surface, a recessed portion disposed on the upper surface, and a plurality of guiding grooves which are equidistantly distributed and vertically downward from the upper surface of the pedestal; and a depth of the plurality of guiding grooves is greater than a depth of the recessed portion.

4. The kit of claim 3, wherein the depth of the plurality of guiding grooves is greater than the depth of the recessed portion by 1.8-2.3 mm, and a spacing between two adjacent guiding grooves is 1 mm.

5. The kit of claim 3, wherein the recessed portion is an ellipsoid with a width of 16 mm and a length of 25 mm; and a vertical distance from a lowest point of the recessed poriton to the upper surface of the pedestal is 8.5 mm.

* * * * *